United States Patent
Nair et al.

(10) Patent No.: US 8,916,240 B2
(45) Date of Patent: Dec. 23, 2014

(54) POROUS ORGANIC POLYMERIC FILMS AND PREPARATION

(71) Applicants: Mridula Nair, Penfield, NY (US); Tamara K. Jones, Rochester, NY (US)

(72) Inventors: Mridula Nair, Penfield, NY (US); Tamara K. Jones, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 122 days.

(21) Appl. No.: 13/686,942

(22) Filed: Nov. 28, 2012

(65) Prior Publication Data

US 2014/0147647 A1    May 29, 2014

(51) Int. Cl.
| | | |
|---|---|---|
| B05D 3/02 | (2006.01) | |
| C09D 101/08 | (2006.01) | |
| A61L 15/22 | (2006.01) | |
| A61L 15/42 | (2006.01) | |
| C08J 5/18 | (2006.01) | |
| C08J 9/00 | (2006.01) | |
| C08J 9/28 | (2006.01) | |
| C08F 2/32 | (2006.01) | |

(52) U.S. Cl.
CPC ............... *C09D 101/08* (2013.01); *B05D 3/02* (2013.01); *C08F 2/32* (2013.01); *A61L 15/225* (2013.01); *A61L 15/425* (2013.01); *C08J 5/18* (2013.01); *C08J 9/0061* (2013.01); *C08J 9/283* (2013.01); *C08J 2201/05* (2013.01); *C08J 2367/04* (2013.01); *C08J 2375/06* (2013.01)
USPC ........................................ 427/385.5; 524/801

(58) Field of Classification Search
None
See application file for complete search history.

(56) References Cited

U.S. PATENT DOCUMENTS

| 4,613,628 | A  | * | 9/1986 | Hoshino et al. ................. 521/72 |
|---|---|---|---|---|
| 5,429,826 | A  | * | 7/1995 | Nair et al. ........................ 424/501 |
| 7,754,409 | B2 | * | 7/2010 | Nair et al. .................... 430/137.14 |
| 8,110,628 | B1 |   | 2/2012 | Nair et al. |
| 2003/0002029 | A1 |   | 1/2003 | Dukler et al. |
| 2008/0176157 | A1 | * | 7/2008 | Nair et al. .................... 430/108.21 |
| 2010/0212928 | A1 |   | 8/2010 | Abe et al. |
| 2012/0027833 | A1 |   | 2/2012 | Zilberman |
| 2012/0167666 | A1 |   | 7/2012 | Nair et al. |

FOREIGN PATENT DOCUMENTS

WO    99/09070    2/1999

OTHER PUBLICATIONS

M. Srinivasarao, et al., "Three-Dimensionally Ordered Array of Air Bubbles in a Polymer Film", Science, vol. 292, Apr. 6, 2001, pp. 79-82.

H. T. Ham., "Macroporous Polymer Thin Film Prepared from Temporarily Stabilized Water-in-Oil Emulsion", J. Phys. Chem B, 2006, 110, pp. 13959-13964.

Liu et al., "Porogen-induced surface modification of nano-fibrous poly(L-lactic acid) scaffolds for tissue engineering," Biomaterials, 27 (2006) 3980-3987.

\* cited by examiner

*Primary Examiner* — Erma Cameron
(74) *Attorney, Agent, or Firm* — J. Lanny Tucker

(57) ABSTRACT

Porous organic polymeric films having multiple discrete cavities can be prepared using an water-in-oil emulsion that includes a cavity stabilizing hydrocolloid on the inner walls of the multiple discrete cavities. The multiple discrete cavities can also include organic catalytic materials for various catalytic reactions, markers materials for security applications, or the multiple discrete cavities can be used to increase opacity, hydrophobicity, or other desirable properties compared to nonporous organic polymeric films composed of the composition and dry thickness.

18 Claims, No Drawings

US 8,916,240 B2

POROUS ORGANIC POLYMERIC FILMS AND PREPARATION

COPENDING APPLICATIONS

Reference is made to copending and commonly assigned U.S. Ser. No. 13/686,941 filed Nov. 28, 2012, by Robello, Nair, Mis, and Dirmyer and entitled SEMI-PERMEABLE PARTICLES HAVING METALLIC CATALYSTS AND USES.

Reference is made to copending and commonly assigned U.S. Ser. No. 13/686,946 filed Nov. 28, 2012, by Mis, Nair, and Robello and entitled PARTICLES CONTAINING ORGANIC CATALYTIC MATERIALS AND USES.

Reference is made to copending and commonly assigned U.S. Ser. No. 13/686,943 filed Nov. 28, 2012, by Nair, Jones, and Mis and entitled POROUS PARTICLES AND METHODS OF MAKING THEM.

FIELD OF THE INVENTION

This invention relates to porous organic polymeric films having small discrete cavities in a continuous polymeric solid phase. This invention also relates to methods for making these porous organic polymeric films.

BACKGROUND OF THE INVENTION

Porous organic polymer films are of interest because of their utility as template materials, selective adsorbents, matrices for cell growth in tissue engineering and wound dressings, membranes in separation process, catalytic supports, lightweight structural materials, dielectric materials for electronic devices and optical materials.

It is known that porous particles can be prepared for various purposes, and some porous particles are designed to have marker materials included within discrete pores, which markers allow the use of the particles for specific detection. For example, U.S. Patent Applications 2008/0176157 (Nair et al.) and 2010/0021838 (Putnam et al.) and U.S. Pat. No. 7,754,409 (Nair et al.) describe porous particles and a method for their manufacture, which porous particles are designed to be toner particles for use in electrophotography.

Still another important use of polymeric particles is as a means for marking documents, clothing, or labels as a "security" tag, for example for authentication of documents using an electrophotographic process and core-shell toner particles containing an infrared emitting component and a detection step. For example, U.S. Patent Application Publication 2003/0002029 (Dukler et al.) describes a method for labeling documents for authentication using a toner particle containing two or more mixed compounds having a characteristic detectable signal.

It is also desirable to have an alternative way of marking documents, clothing, or labels with a "security" tag, for authentication of documents using an easier process than use of porous particles containing markers. Product counterfeiting occurs in artworks, CD's, DVD's, computer software recorded on various media, perfumes, designer clothes, handbags, luggage, automobile and airplane parts, securities (for example stock certificates), identification cards (for example, drivers' licenses, passports, visas, and green cards), credit and debit cards, smart cards, and pharmaceuticals. The application of a security marker or taggant to an object or product for authenticating the origin or intended market is known in the art. Security markers can be incorporated into components that make up the object or product, or they can be incorporated into papers, inks, or varnishes that are applied to the object or product, or they can be incorporated into labels affixed to the object, product, or packaging there for. The presence of the security marker can be used to verify the authenticity of the origin of the object using suitable detection means that is specific to the security marker.

Some security markers can be dispersed within a carrier varnish and are referred to as particle-based or pigment-based markers. Such markers remain intact in the varnish and will appear as particles when examined microscopically. Other security markers are dissolvable in an ink or varnish and distributed in the carrier on a molecular level. These markers are not readily detected with a microscope and require more sophisticated detection equipment.

A means for detecting a population of microparticles is described in U.S. Pat. No. 5,450,190 (Schwartz et al.). Groups of microparticles of specific sizes and fluorescent properties or colors are mixed with toner particles and the resulting mixture is used in laser printer cartridges or photocopy machines to provide detectable images.

Particles having two or more different light emitting species can also be printed onto various substrates using various printing means, as described in WO 2007/051035 (Haushalter).

Toner particles having a luminescent material that includes quantum dots are described in EP 2,025,525 (Wosnick et al.) and can be used to form detectable markings on substrates. These toner particles can also include colorants or other detectable components.

Porous particles containing various markers that can be used for specific means of detection are also described in U.S. Pat. No. 8,110,628 (Nair et al.) and U.S. Patent Application Publication 2012/0167666 (Nair et al.) describes porous particles and articles containing same that contain various marker materials within discrete pores for specific means of detection. These porous particles can be prepared using multiple water-in-oil emulsions containing the desired markers and pore stabilizing hydrocolloids to prevent coalescence.

Known methods for the preparation of porous polymer films include the breath figure method to create porous films having uniform pore sizes as described in Science 2001, 292, 79. This method utilizes the condensation of water vapor on the surface of a polymer solution in an organic solvent as droplets that self-assemble at the air-solution interface and, upon evaporation of the solvents, porous polymer structures are obtained. However, this method requires precise control over the processing environment during the fabrication process.

Water-in-oil emulsions where aqueous droplets are dispersed in organic solution of a polymer have been used to make porous films. (J. Phys. Chem. B 2006, 110, 13959-13). Dip-coating the emulsion onto a glass slide and air-drying led to porous polymer thin films. However, such emulsions were only temporarily stabilized and the process was not practical or easily scaled to greater quantities.

U.S. Patent Application Publication 2010/0212928 (Abe et al.) describes the use of water-in-oil emulsions to create organic porous materials as an insulating material around a conductor to provide an insulated wire or cable.

Drug-eluting films loaded with bioactive agents are described in U.S. Patent Application 2012/0027833 (Zilberman). These films are porous and can be prepared by freeze drying a water-in-oil emulsion.

In spite of all the known methods, there still exists a need for a one-step practical, and scalable method for making thin porous organic polymeric films, either as free standing films or films coated onto a substrate for various uses described above. In particular, it would be desirable to have a water-in-oil emulsion that is stable over time that is useful to enable a manufacturable process for creating porous organic polymeric films.

In addition, it would be useful to have porous organic polymeric films that contain various detectably different markers so the films can be used in various security applications.

SUMMARY OF THE INVENTION

The present invention provides a porous organic polymeric film comprising a water-insoluble polymer that provides a continuous polymeric solid phase, and multiple discrete cavities having inner walls and that are uniformly dispersed within the continuous polymeric solid phase, wherein the porous organic polymeric film further comprises a cavity stabilizing hydrocolloid on the inner walls of the multiple discrete cavities.

This invention also provides a method for preparing a porous organic polymeric film, the method comprising:

providing: (a) an aqueous phase comprising a cavity stabilizing hydrocolloid, and (b) an oil phase comprising a water-insoluble polymer or polymer precursor and an organic solvent, dispersing the aqueous phase in the oil phase to form a water-in-oil emulsion, applying the water-in-oil emulsion to a substrate to form a liquid coating containing droplets of the aqueous phase in the oil phase, and removing the organic solvent from the oil phase and water from the aqueous phase, and polymerizing the polymer precursor if present, to form a porous organic polymeric film comprising a continuous polymeric solid phase, and multiple discrete cavities having inner walls and that are uniformly dispersed within the continuous polymeric solid phase, wherein the porous organic polymeric film further comprises the cavity stabilizing hydrocolloid on the inner walls of the multiple discrete cavities.

The present invention provides a number of advantages such as providing porous organic polymeric films using a single-step method that is practical and easily used in manufacturing. The method of this invention can accommodate many different classes of polymers from which porous organic polymeric membranes can be derived. The method of this invention can also utilize various additives in the discrete cavities, including but not limited to, organic or inorganic catalysts, marker particles, bioactive agents, magnetic particles, nanoparticles and other described below.

DETAILED DESCRIPTION OF THE INVENTION

Definitions

As used herein to define various components of the laser-engraveable compositions, formulations, and layers, unless otherwise indicated, the singular forms "a", "an", and "the" are intended to include one or more of the components (that is, including plurality referents).

Each term that is not explicitly defined in the present application is to be understood to have a meaning that is commonly accepted by those skilled in the art. If the construction of a term would render it meaningless or essentially meaningless in its context, the term's definition should be taken from a standard dictionary.

The use of numerical values in the various ranges specified herein, unless otherwise expressly indicated otherwise, are considered to be approximations as though the minimum and maximum values within the stated ranges were both preceded by the word "about". In this manner, slight variations above and below the stated ranges can be used to achieve substantially the same results as the values within the ranges. In addition, the disclosure of these ranges is intended as a continuous range including every value between the minimum and maximum values.

Unless otherwise indicated, the terms "porous organic polymeric films" and "porous films" are meant to refer to embodiments of the present invention.

In this invention, the term "cavity" is used instead of "pore" to define a void within the continuous polymeric phase of the porous organic polymeric films. Cavities can be interconnected to form a network of voids or they can exist in isolation from other cavities.

The porous organic polymeric films can include "micro", "meso", and "macro" discrete cavities, which according to the International Union of Pure and Applied Chemistry, are the classifications recommended for discrete cavities less than 2 nm, from 2 nm to 50 nm, and greater than 50 nm, respectively. The porous organic polymeric films can include closed discrete cavities of all sizes and shapes (cavities entirely within the continuous polymeric phase). There may be open cavities on the surface of the porous organic polymeric film, which open cavities are formed during the coating and drying process. The thickness of the porous organic polymeric film, the formulation, and manufacturing conditions are the primary controlling factors for discrete cavity size.

The multiple discrete cavities in the porous organic polymeric films can have an average size of at least 200 nm and up to and including 5 µm or typically at least 500 nm and up to and including 3 µm. For spherical discrete cavities, this average size is an "average diameter". For non-spherical discrete cavities, the average size refers to the average largest dimension". The multiple discrete cavities can have the same or different average sizes. Discrete cavity size can be determined by analyzing Scanning Electron Microscopy (SEM) images of cross-sectional images using a commercial statistical analysis software package. For example, the "average" discrete cavity size can be determined by calculating the average diameter of 20 measured discrete cavities.

Uses

The porous organic polymeric films of this invention can be used for various industrial, medical, and optical applications. For example, they can be used as synthetic tissue engineering scaffolds as well as drug delivery devices. They can also be used as templates for various chemical and electrochemical reactions where the porous film is removed after the reaction is carried out. Optical uses are also possible since the porous films have an increased opacity compared to nonporous films prepared from the same polymers. Such porous films can be useful as catalytic surfaces and supports, adsorbents, chromatographic materials, membranes, light-weight structural materials, and thermal, acoustic and electrical insulators, and fuel cell membranes.

The porous organic polymeric films of this invention can also be used in security systems for detection of counterfeits, document authentication, and labeling of consumer goods (such as designer clothes, handbags, perfumes, and cosmetics). They can also be used in paper and plastic cards, for example driver's licenses, passports, and other identification cards. Moreover, the porous organic polymeric films can be incorporated into or used as packaging and packaging components such as fabrics, labels, polymeric films, fibers, tape, foils, paperstock, and cardboard packing.

Method for Preparing Porous Organic Polymeric Films

The porous organic polymeric films are prepared using stabilized water-in-oil emulsions by coating them onto a substrate and drying or otherwise solidifying the liquid coating using known methods (described below). Suitable film-forming polymers or polymer precursors (both described below) are incorporated in an oil phase (or the polymer precursors can be the oil phase), and a suitable water phase containing appropriate cavity stabilizing hydrocolloids (described below) is dispersed in the oil phase to form the water-in-oil emulsion. Water droplets dispersed within the oil phase act as templates for the resulting multiple discrete cavities in the dried porous film. Certain cavity stabilizing hydrocolloids or low HLB emulsifiers (both described below) are used to stabilize the water droplets to control the size of the discrete cavities.

More particularly, an aqueous phase (primarily water as a solvent) is formed having dissolved therein, one or more cavity stabilizing hydrocolloids (described below). The one or more cavity stabilizing hydrocolloids can be present in this first aqueous phase in an amount of at least 0.5 weight % and up to and including 20 weight %, or typically of at least 1 weight % and up to and including 10 weight %, all based on the total first aqueous phase weight.

The aqueous phase can also comprise a buffering salt, catalyst, colorant, release agent, bioactive agent, or any combination of these materials.

One or more cavity stabilizing hydrocolloids are generally disposed on the inner walls within at least some of the multiple discrete cavities, that is, at the interface of the multiple discrete cavities and the continuous polymeric phase of the resulting porous organic polymeric film, and typically, these compounds are disposed within essentially all (at least 95%) of the multiple discrete cavities. Suitable cavity stabilizing hydrocolloids include but are not limited to, both naturally occurring and synthetic, water-soluble or water-swellable polymers selected from the group consisting of cellulose derivatives [such as for example, carboxymethyl cellulose (CMC) that is also referred to as sodium carboxymethyl cellulose], gelatin (for example, alkali-treated gelatin such as cattle bone or hide gelatin, or acid treated gelatin such as pigskin gelatin), gelatin derivatives (for example, acetylated gelatin and phthalated gelatin), proteins and protein derivatives, hydrophilic synthetic polymers [such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, and methacrylamide copolymers], water soluble microgels, polyelectrolytes [such as a polystyrene sulfonate, poly(2-acrylamido-2-methylpropanesulfonate), and a polyphosphate], and mixtures of any of these classes of materials.

In order to stabilize the water-in-oil emulsions so that they can be held without ripening or coalescence, it is desired that the cavity stabilizing hydrocolloids in the aqueous phase have a higher osmotic pressure than that of the oil phase depending on the solubility of water in the oil. This reduces the diffusion of water into the oil phase from the aqueous phase and thus reduces the ripening caused by migration of water between the water droplets. One can achieve a higher osmotic pressure in the aqueous phase either by increasing the concentration of the cavity stabilizing hydrocolloid or by increasing the charge on the cavity stabilizing hydrocolloid (the counter-ions of the dissociated charges on the cavity stabilizing hydrocolloid increase its osmotic pressure). It can be advantageous to have weak base or weak acid moieties in the cavity stabilizing hydrocolloids that allow for their osmotic pressures to be controlled by changing the pH. Such cavity stabilizing hydrocolloids are considered "weakly dissociating hydrocolloids". For these weakly dissociating hydrocolloids, the osmotic pressure can be increased by buffering the pH to favor dissociation, or by simply adding a base (or acid) to change the pH of the aqueous phase to favor dissociation. One example of such a weakly dissociating hydrocolloid is CMC that has a pH sensitive dissociation (the carboxylate is a weak acid moiety). For CMC, the osmotic pressure can be increased by buffering the pH, for example using a pH 6-8 buffer, or by simply adding a base to raise the pH of the aqueous phase to favor dissociation. For aqueous phases containing CMC, the osmotic pressure increases rapidly as the pH is increased from 4-8.

Other synthetic polyelectrolyte hydrocolloids such as polystyrene sulfonate, poly(2-acrylamido-2-methylpropanesulfonic acid, alkali metal salt), and polyphosphates are also useful cavity stabilizing hydrocolloids.

For example, particularly useful cavity stabilizing hydrocolloids include but are not limited to, carboxymethyl cellulose (CMC), a gelatin or gelatin derivative, a protein or protein derivative, a hydrophilic synthetic polymer, a water-soluble microgel, a polystyrene sulfonate, poly(2-acrylamido-2-methylpropanesulfonate), a polyphosphate, and mixtures thereof.

An oil phase is also provided, which comprises one or more water-insoluble polymers or polymer precursors and optionally one or more amphiphilic block copolymers (described below) in a suitable organic solvent (or mixtures of organic solvents described below).

Useful water-insoluble polymers include but are not limited to, those derived from vinyl (unsaturated) monomers such as styrene monomers and condensation polymers and mixtures thereof. Such water-insoluble polymers include but are not limited to, homopolymers and copolymers such as polyesters, styrenic polymers (for example polystyrene and polychlorostyrene), mono-olefin polymers (for example, polymers formed from one or more of ethylene, propylene, butylene, and isoprene), vinyl ester polymers (for example, polymer formed from one or more of vinyl acetate, vinyl propionate, vinyl benzoate, and vinyl butyrate), acrylic polymers for example formed from one or more α-methylene aliphatic monocarboxylic acid esters (for example, polymers formed from one or more of methyl acrylate, ethyl acrylate, butyl acrylate, dodecyl acrylate, octyl acrylate, phenyl acrylate, methyl methacrylate, ethyl methacrylate, butyl methacrylate, and dodecyl methacrylate), vinyl ether polymers (such as polymers formed from one or more of vinyl methyl ether, vinyl ethyl ether, and vinyl butyl ether), vinyl ketone polymers (for example, polymers formed from one or more of vinyl methyl ketone, vinyl hexyl ketone, and vinyl isopropenyl ketone), and aliphatic cellulose ester polymers. Particularly useful water-insoluble polymers include polystyrenes (including homopolymers and copolymers of styrene derivatives), polyesters, styrene/alkyl acrylate copolymers, styrene/alkyl methacrylate copolymers, styrene/acrylonitrile copolymers, styrene/butadiene copolymers, styrene/maleic anhydride copolymers, polyethylene resins, and polypropylene resins. Other useful water-insoluble polymers include polyurethanes, urethane acrylic copolymers, epoxy resins, silicone resins, polyamide resins, modified rosins, paraffins, and waxes. Still other useful water-insoluble polymers are polyesters of aromatic or aliphatic dicarboxylic acids with one or more aliphatic diols, such as polyesters of isophthalic or terephthalic or fumaric acid with diols such as ethylene glycol, cyclohexane dimethanol, bisphenol adducts of ethylene or propylene oxides, and aliphatic polyesters such as polycaprolactone, polylactic acid, polyglycolic acid, and block and graft copolymers derived from them. The polyesters can be saturated or unsaturated.

Particularly useful water-insoluble polymers are selected from polyesters, styrenic polymers (such as styrene/acrylate copolymers, styrene/alkyl methacrylate copolymers), mono-olefin polymers, vinyl ester polymers, α-methylene aliphatic monocarboxylic acid ester polymers, vinyl ether polymers, vinyl ketone polymers, and aliphatic cellulose ester polymers. Particularly useful water-insoluble polymers include styrene-butyl acrylate copolymers, polycaprolactone, polyurethanes, and bisphenol-A polyester. In some embodiments, the water-insoluble polymer used in the oil phase has a low acid number.

In other embodiments, the polymer is formed from one or more ethylenically unsaturated polymerizable monomers such as an ethylenically unsaturated polymerizable monomer selected from vinyl monomers and acrylic monomers. These monomers are included within the oil phase and can be polymerized using useful polymerization initiators.

Thus, in the method of this invention, the water-insoluble polymers described above can be replaced with one or more ethylenically unsaturated polymerizable monomers (generally in liquid form) as polymer precursors and a polymerization initiator to form the water-in-oil emulsion. Thus, the oil phase can comprise predominantly the ethylenically unsaturated polymerizable monomers as the organic solvents. The ethylenically unsaturated polymerizable monomers can be polymerized for example through the application of heat or radiation (such as actinic or IR radiation) after coating the emulsion on a substrate, before or after any organic solvents are removed to form one or more suitable water-insoluble polymers.

In addition, if desired, the water-immiscible ethylenically unsaturated polymerizable monomer(s) can be used in mixture with one or more water-insoluble polymers as described above to achieve the desired continuous polymeric phase.

Ethylenically unsaturated polymerizable monomers useful in this invention include but are not limited to, monofunctional and polyfunctional monomers such as acrylates and methacrylates, vinyl monomers, for example methyl methacrylate, butyl acrylate, styrene, vinyl pyrrolidone, divinyl benzene, ethylene glycol dimethacrylate, trimethylolpropane triacrylate, hexanediol dimethacrylate, tripropylene glycol dimethacrylate, diethylene glycol dimethacrylate, pentaerythritol triacrylate, dipentaerythritol hexamethacrylate, and neopentyl glycol di(meth)acrylate, and mixtures thereof. It is also within the scope of this invention to use ethylenically unsaturated polymerizable oligomers in place of or in addition to the ethylenically unsaturated polymerizable monomers described above.

To provide additional stability of multiple discrete cavities in the water-in-oil emulsions and resulting porous organic polymeric films, the oil phase can also comprise low HLB polymeric emulsifiers preferably, one or more amphiphilic (low HLB) block copolymers (emulsifiers) that are disposed at the interface of the multiple discrete cavities and the continuous polymeric solid phase of the porous organic polymeric film. The term "amphiphilic" is generally used to refer to a molecule having a polar, water-soluble group that is attached to a non-polar, water-insoluble hydrocarbon or oleophilic group. "HLB" refers to the well known term "hydrophilic-lipophilic balance" and refers to the measure of the degree to which a compound is hydrophilic or lipophilic and is determined for a given polymer or molecule using the known Griffin's mathematical method where HLB equals 20 $(M_h/M)$ wherein $M_h$ equals the molecular weight of the hydrophilic block in the molecule and M equals the molecular weight of the whole block copolymer. Thus, the amphiphilic block copolymers useful in the present invention have a low HLB value, meaning that they are more lipophilic than hydrophilic, and they comprise both water-soluble blocks (hydrophilic) and water-insoluble blocks (lipophilic), and the HLB value is less than or equal to 6.

The molecular weights of the water-soluble component and the oleophilic components are not critical as long as the resulting amphiphilic block copolymer has an HLB equal to or less than 6. For example, the block copolymers can have a hydrophilic block having a molecular weight $(M_h)$ of at least 100 and up to and including 25,000, and a hydrophobic (or oleophilic) block having a molecule weight $(M_n)$ of at least 500 to and including 100,000.

In some embodiments, the amphiphilic block copolymer comprises a hydrophilic segment comprising polyethyleneoxide and a hydrophobic (oleophilic) segment comprising polycaprolactone. Further details of such block copolymers are provided in Kowalski et al., *Macromol. Rapid Commun.*, 1998, Vol. 19, 567, and in U.S. Pat. No. 5,429,826 (Nair et al.) that is incorporated herein by reference.

Other useful hydrophilic components for amphiphilic block copolymers can be derived from poly(2-ethyloxazolines), poly(saccharides), and dextrans.

The oleophilic block component of the amphiphilic block copolymers useful in the present invention can also be selected from many common components, including but not limited to, oleophilic components derived from monomers such as: styrene, caprolactone, propiolactone, β-butyrolactone, δ-valerolactone, ε-caprolactam, lactic acid, glycolic acid, hydroxybutyric acid, lysine and its derivatives, and glutamic acid and its derivatives. Particularly useful oleophilic components of the amphiphilic block copolymers useful in this invention are derived from polymers such as certain polyesters, polycarbonates, and polyamides, or more particularly polyesters such as poly(caprolactone) and its derivatives, poly(lactic acid), poly(3-hydroxybutyrate-co-3-hydroxyvalerate), poly(3-hydroxybutyrate), and poly(glycolic acid).

A particularly useful amphiphilic block copolymer can be defined as an A-B block copolymer that comprises a hydrophilic block (A) comprising polyethyleneoxide and a hydrophobic (oleophilic) block (B) comprising polycaprolactone represented herein as PEO-b-PCL.

The amphiphilic block copolymers can also be represented as "A-B-A" type wherein A and B are defined above. Although this invention is directed mainly towards the use of amphiphilic block copolymers, graft copolymers and random graft copolymers containing similar components are also useful.

The amphiphilic block copolymer can be present in the resulting porous organic polymeric films in an amount of at least 1 weight % and up to and including 99.5 weight %, or at least 2 weight % and up to and including 50 weight %, based on total porous film dry weight. It is contemplated that in some embodiments, the amphiphilic block copolymer can comprise the continuous polymeric solid phase of the porous particles and at the same time, function as the low HLB material that is disposed at the interface of the multiple discrete cavities.

In the method of this invention, the amphiphilic block copolymer can be present in the oil phase in an amount of at least 0.2 weight % and up to and including 30 weight %, or typically of at least 0.5 weight % and up to and including 15 weight %, based on the total oil phase weight.

While low HLB amphiphilic block copolymers are preferred as the optional emulsifiers for preparing the water-in-oil emulsions, other polymeric emulsifiers are also envisioned as useful depending on the composition of the oil phase. An example of such an emulsifier is GRINDSTED® PGPR 90, polyglycerol polyricinolate emulsifier, obtained from Dupont.

Any suitable organic solvent that will dissolve the water-insoluble polymers (or polymer precursors) and that is also immiscible with water can be used to prepare the oil phase used in forming the water-in-oil emulsion. Such organic solvents include but are not limited to, ethyl acetate, propyl acetate, chloromethane, dichloromethane, vinyl chloride, trichloromethane, carbon tetrachloride, ethylene chloride, trichloroethane, toluene, xylene, cyclohexanone, 2-nitropropane, dimethyl carbonate, and mixtures of two or more of these solvents. Ethyl acetate and propyl acetate are generally good solvents for many useful water-insoluble polymers while being sparingly soluble in water, and they are readily removed as described below by evaporation.

The aqueous phase is then dispersed in the oil phase comprising one or more polymers (or polymer precursors) that eventually form a continuous polymeric solid phase, to form a water-in-oil emulsion. These polymer(s) are dissolved in the organic solvent(s). The aqueous phase creates the multiple discrete cavities in the resulting porous organic polymeric films.

Salts can be added to the aqueous phase to buffer the resulting water-in-oil emulsion and optionally to control the osmotic pressure of the aqueous phase. When CMC is used as a cavity stabilizing hydrocolloid, for example, the osmotic pressure can be increased by using inorganic salts or a pH 7 buffer. The water-in-oil emulsion can also contain additional cavity forming agents such as ammonium bicarbonate.

Depending upon the ultimate use of the porous organic polymeric films, the water-in-oil emulsion can also include various additives, which are added to the oil or the aqueous phase. Such additives can include but are not limited to, colorants, charge control agents, compatibilizers, wetting agents, surfactants, lubricants, plasticizers, and release agents such as waxes and lubricants. Combinations of these materials can also be used.

The water-in-oil emulsion can be prepared by any known emulsifying technique and conditions using any type of mixing and shearing equipment. Such equipment includes but is not limited to, a batch mixer, planetary mixer, single or multiple screw extruder, dynamic or static mixer, colloid mill, high pressure homogenizer, sonicator, or a combination thereof. While any high shear type agitation device is useful, a particularly useful homogenizing device is the Microfluidizer® such as Model No. 110T produced by Microfluidics Manufacturing operating at >5000 psi. In this device, the droplets of the aqueous phase can be dispersed and reduced in size in the oil phase in a high flow agitation zone and, upon exiting this zone, the size of the droplets of the dispersed aqueous phase is reduced to uniform sized dispersed droplets in the oil phase. The temperature of the process can be modified to achieve the optimum viscosity for emulsification of the aqueous phase droplets and to minimize evaporation of the organic solvent(s).

The porous organic polymeric films of the invention are prepared by coating or otherwise applying a stabilized water-in-oil emulsion onto a substrate to form a liquid precursor porous organic polymeric film by any of a number of well known techniques, such as dip coating, wrapped wire rod coating, blade coating, spray coating, air knife coating, gravure coating and reverse roll coating, slot coating, extrusion hopper coating, slide coating, curtain coating, and other techniques that would be readily apparent to one skilled in the art.

After application of the stabilized water-in-oil emulsion to the substrate, the liquid precursor porous organic polymeric film is generally dried by simple evaporation of the organic solvents from the oil phase and water from the multiple discrete cavities, which drying can be accelerated by known techniques such as convection heating to provide a solidified porous organic polymeric film.

In some embodiments, the method of this invention further comprises removing the water from the aqueous phase droplets of the liquid precursor porous organic polymeric film before or after removing the organic solvent from the oil phase.

Representative application and drying methods are described in further detail in *Research Disclosure No. 308119*, December 1989, pages 1007-1008. When the oil phase is made up of polymer precursors such as ethylenically unsaturated polymerizable monomers, they can be polymerized for example through the application of heat or radiation (such as actinic or IR radiation) after application of the water-in-oil emulsion and before or after removal of any organic solvents, to form a solidified porous organic polymeric film.

Depending on the application two or more stabilized water-in-oil emulsions can be mixed prior to coating or applying onto the substrate. The water-in-oil emulsions may have the same or compositionally different water phases and oil phases. While the oil phases can mix to provide one compositionally continuous oil phase, the water phases can remain distinct resulting in a porous organic polymeric film with detectably different cavities of similar or different sizes in the final porous organic polymeric film. The distinguishing characteristics can simply be the presence cavities of two different sizes for instance or different markers in discrete cavities of the same or different sizes.

The substrates onto which the solidified porous organic polymeric films of this invention can be formed by coating the respective water-in-oil emulsions can comprise various polymeric films, such as films derived from triacetyl cellulose, polyethylene terephthalate (PET), diacetyl cellulose, acetate butyrate cellulose, acetate propionate cellulose, polyether sulfone, polyacrylic based resin (for example, polymethyl methacrylate), a polyurethane-based resin, polyester, polycarbonate, aromatic polyamide, polyolefins (for example, polyethylene and polypropylene), polymers derived from vinyl chloride (for example, polyvinyl chloride and a vinyl chloride/vinyl acetate copolymer), polyvinyl alcohol, polysulfone, polyether, polynorbornene, polymethylpentene, polyether ketone, (meth)acrylonitrile, paper, glass, Teflon, and other materials that would be apparent to one skilled in the art. The substrates can vary in thickness, for example, at least 0.00254 cm to and including 0.127 cm.

Depending on the use being considered, the particular substrate can contain an undercoat or primer (polymeric subbing) layer between the support and the porous organic polymeric film. Subbing layers that are used to promote the adhesion of applied compositions to a substrate support are well known in the art and any such compositions can be used. Some useful subbing compositions include but are not limited to polymers derived from vinylidene chloride such as vinylidene chloride/methyl acrylate/itaconic acid terpolymers and vinylidene chloride/acrylonitrile/acrylic acid terpolymers. These and other suitable subbing compositions are described, for example, in U.S. Pat. Nos. 2,627,088, 2,698,240, 2,943,937, 3,143,421, 3,201,249, 3,271,178, 3,443,950, and 3,501,301 all of which are incorporated herein by reference. A polymeric subbing layer can additionally be overcoated with a second subbing layer comprised of gelatin, typically referred to as a "gel sub".

Film and paper substrates can be surface treated by various processes including corona discharge, glow discharge, UV or ozone exposure, flame, or solvent washing in order to promote adhesion of coating compositions.

In the case of free-standing porous organic polymeric films, a water-in-oil emulsion can be coated on an untreated or uncoated substrate and then peeled off.

Porous Organic Polymeric Films

The porous organic polymeric films resulting from the method of this invention therefore comprise one or more polymers (as described above) that provide a continuous polymeric solid phase. Multiple discrete cavities having inner walls are uniformly dispersed within the continuous polymeric solid phase. Since the cavity stabilizing hydrocolloids (described above) are present in the aqueous phase used to make the water-in-oil emulsion, these materials are then present on the inner walls of the multiple discrete cavities, generally in an amount of at least 0.5 weight % and up to and including 20 weight %, based on the total solid porous organic polymeric film dry weight.

If used in the method, the low HLB emulsifiers such as the low HLB amphiphilic block copolymers described above, are also disposed at the interface of the multiple discrete cavities and the continuous polymeric solid phase in the porous organic polymeric films, in an amount of at least 1 weight % up to and including 99.5 weight %, based on total porous organic polymeric film dry weight. Particularly useful low HLB amphiphilic block copolymers comprise a hydrophilic segment comprising polyethyleneoxide and an oleophilic segment comprising polycaprolactone.

The thickness of the porous organic polymeric film will depend upon its field of use. For example, the porous organic polymeric film of this invention can have an average dry thickness of at least 2 μm and up to and including 500 μm. This parameter is determined by measuring the dry thickness in at least 5 different places of a film sample using a Keyence laser triangulation head with a spot size of 25 μm.

In many embodiments, the multiple discrete cavities in the porous organic polymeric film have an average size of at least 30 nm and up to and including 30 μm, or more likely, they can have an average size of at least 100 nm and up to and including 5 μm or more typically at least 500 nm and up to and including 3 μm. For spherical discrete cavities, this average size is an "average diameter". For non-spherical discrete cavities, the average size refers to the average largest dimension". The multiple discrete cavities can have the same or different average sizes. Discrete cavity size can be determined from representative scanning electron micrographs of the porous organic polymeric films and simple image analysis routines were used to first identify the discrete cavities within and then to measure the diameter of the multiple discrete cavities. A commercial statistical analysis software package can be used to study the distribution of the discrete cavities within each porous organic polymeric film. For example, the "average" discrete cavity size can be determined by calculating the average diameter of 20 measured discrete cavities.

In general, the total volume of the multiple discrete cavities in the porous organic polymeric film is at least 5% and up to and including 80%, or more likely at least 15% and up to and including 60% based on the total dry porous organic polymeric film volume. This porosity can be measured by the mercury intrusion technique.

Particularly useful porous organic polymeric films are composed of a water-insoluble polymer that is a styrene-butyl acrylate copolymer, polycaprolactone, polyurethane, or bisphenol-A polyester.

In addition, a porous organic polymeric film of this invention can be disposed on a suitable substrate such as polymeric films, for example those derived from triacetyl cellulose, polyethylene terephthalate (PET), diacetyl cellulose, acetate butyrate cellulose, acetate propionate cellulose, polyether sulfone, polyacrylic-based resin [for example, poly(methyl methacrylate)], a polyurethane-based resin, polyester, polycarbonate, aromatic polyimide, polyolefins (for example, polyethylene and polypropylene), polymers derived from vinyl chloride (for example, polyvinyl chloride and a vinyl chloride/vinyl acetate copolymer), polyvinyl alcohol, polysulfone, polyether, polynorbornene, polymethylpentene, polyether ketone, (meth)acrylonitrile, paper, glass, and Teflon. The porous organic polymeric films can also be removed from a substrate to form free standing porous organic polymeric films.

In some embodiments, the porous organic polymeric film has a reflectance that is at least 6 times greater than the reflectance of a nonporous organic polymeric film of the same composition and dry thickness. The opposite effect would be observed for transmission through the porous organic polymeric film.

In some embodiments of this invention, at least some of the multiple discrete cavities in the porous organic polymeric film comprise an aqueous solution or suspension of an organic catalytic material, wherein the solid porous organic polymeric film is impermeable to the organic catalytic material, and the solid porous organic polymeric film is permeable to molecules having a molar mass that is 1000 Daltons or less.

Useful organic catalytic materials are enzymes, such as catalase, peroxidase, superoxide dismutase, carbonic anhydrase, cytochrome P450, alcohol dehydrogenase, aspartate aminotransferase, luciferase, hydrolase, glucose oxidase, glucose isomerase, trypsin, papain, protease, lipase, esterase, urease, cellulase, amylase, lactase, phytase, amidase, thermolysin, diacetyl reductase, and nitrile hydrolase.

In other embodiments, the porous organic polymeric film of the invention, have in at least some of the multiple discrete cavities, nanoparticles of catalytically active metallic materials, which nanoparticles (a) comprise one or more elements selected from Groups 8, 9, 10, and 11 of the Periodic Table, and (b) have an effective diameter of at least 1 nm and up to and including 200 nm.

Useful catalytically active metallic materials include but are not limited to, iron, cobalt, nickel, copper, ruthenium, palladium, rhodium, silver, osmium, iridium, platinum, and gold. Nanoparticles of catalytically active metallic materials comprising palladium, platinum, rhodium, ruthenium, nickel, cobalt, iron, copper, silver, gold, iridium, and osmium are particularly useful in the discrete cavities, and nanoparticles of catalytically active metallic materials comprising palladium, platinum, or nickel are most useful. The catalytically active metallic materials can comprise the described metallic elements as well as compounds comprising the metal elements such as metal alloys (such as an alloy of copper and chromium), metal oxides (such as platinum oxide, osmium oxide, and iron oxide), and metal sulfides (such as nickel sulfide, and iron sulfide). In some embodiments, the aqueous slurry of multiple semi-permeable particles of this invention comprise one or more nanoparticles of catalytically active metallic materials comprising palladium, platinum, rhodium, ruthenium, nickel, cobalt, iron, copper, silver, gold, iridium, and osmium.

The catalytically active metallic materials generally have an effective diameter of at least 1 nm and up to and including 200 nm, typically at least 2 nm and up to and including 100 nm, or at least 2 nm and up to and including 50 nm. These dimensions are meant to define the term "nanoparticles".

In some embodiments, the porous organic polymeric film of this invention comprise nanoparticles of catalytically active metallic materials comprising palladium, platinum, or nickel in the discrete cavities, the nanoparticles having an effective diameter of at least 2 nm and up to and including 100 nm.

The terms "detectably different" or "detectably distinct" refer to different marker materials (or different mixtures of marker materials described below) being detectable from each other using suitable detection means.

As used in this disclosure, the term "isolated from each other" refers to the first and second marker materials being in different (distinct) cavities. In other words, the first marker material is only in certain (first) cavities and the second marker material is present only in different (second) cavities. Each of these sets of cavities can include other marker materials or materials that do not behave as marker materials as long as the first and second marker materials are purposely not located within the same cavities. Another way of defining this feature is that the first marker materials are in the first discrete cavities exclusively and the second marker materials are in the second discrete cavities exclusively.

The terms "first discrete cavity" and "second discrete cavity" refer to different isolated cavities in the porous particle containing different marker materials. These first and second discrete cavities can refer to distinct individual pores, or in most embodiments, they refer to distinct sets of cavities. Each set of cavities includes a plurality of cavities, which cavities are isolated from each other, and the cavities of each set of cavities are isolated from all other cavities of the other sets of cavities in the porous organic polymeric film. The first discrete cavities contain a first marker material and the second discrete cavities contain a second marker material, and any additional discrete cavities can contain still a different marker material. The word "discrete" is also used to define different droplets of the first and second aqueous phases when they are suspended in the oil (solvent) phase (described below).

As described above, the porous organic polymeric film can include two or more marker materials that are detectably different. For convenience, when two detectably different marker materials, they are labeled "first" and "second" marker materials to distinguish them.

As defined herein, the first marker material is present in a first discrete cavity, a second marker material is present in a second discrete cavity, and additional marker materials are present in additional discrete cavities of the porous organic polymeric film. These additional discrete cavities can have an additional detectably different marker material.

In some embodiments, either the first or second discrete cavities contain a marker material but the other set of discrete cavities are "empty" (no marker material).

The detectably different marker materials can be different colored dyes or pigments (or colorants), or metallic pigments, that are generally not water soluble. Such colorants can include but not limited to, those described in U.S. Reissue patent 31,072 (Jadwin et al.) and in U.S. Pat. No. 4,160,644 (Ryan), and U.S. Pat. No. 4,416,965 (Sandhu et al.), U.S. Pat. No. 4,414,152 (Santilli et al.), such as carbon black, Aniline Blue, Calcoil Blue, Chrome Yellow, Ultramarine Blue, Du Pont Oil Red, Quinoline Yellow, Methylene Blue Chloride, Phthalocyanine Blue, Malachite Green Oxalate, Lamp Black, Rose Bengal, C.I. Pigment Red 48:1, C.I. Pigment Red 122, C.I. Pigment Red 57:1, C.I. Pigment Yellow 97, C.I. Pigment Yellow 12, C.I. Pigment Yellow 17, C.I. Pigment Blue 15:1, and C.I. Pigment Blue 15:3. Other useful colorants are described in U.S. Pat. No. 5,385,803 (Duff et al.) and EP 2,025,525 (Wosnick et al.) that are incorporated herein by reference. The marker materials can vary in water solubility although most have little water-solubility. Each marker material can include mixtures of colorants as long as the mixtures of marker materials in the porous organic polymeric film are detectably different. Thus, either or both of the first and second marker materials can be mixtures of marker materials as long as the mixtures are detectably different.

Other classes of marker materials useful in the practice of this invention as first and second marker materials include but are not limited to, different fluorescing materials, radioisotopes, particles of metals and metal-containing compounds (such as metal oxides, metal sulfides, and metal oxyhydroxides) having different magnetic moments, luminescing compounds, as well as bioactive materials. Certain reactive chemicals can be used as markers and kept separate in discrete pores until their reaction is needed. Examples of such reactive chemicals include acids and bases, and isocyanates and amines.

Examples of useful fluorescing marker materials include but are not limited to, compounds that absorb radiation (excite) in the UV and visible regions of the electromagnetic spectrum but then emit or fluoresce in the infrared or visible region of the electromagnetic spectrum. Other useful fluorescing marker materials absorb radiation (excite) in the infrared region and also fluoresce in the infrared region. Still other fluorescing marker materials absorb (excite) in the infrared region and fluoresce in the visible region. Fluorescent light activated dyes can be invisible to or exhibit one color under ambient light conditions and a second color under fluorescent light conditions. Fluorescent dyes are known to the person skilled in the art. Examples of such compound include but are not limited to, coumarins, perylenes, naphthalimides, cyanines including metal phthalocyanines and metal naphthocyanines, xanthenes, oxazines, anthracene, naphthacene, anthraquinone, and thiazine dyes and derivatives thereof so as to make them water-soluble or water-dispersible.

Examples of useful emissive inorganic marker materials include but are not limited to, $CaWO_4$:Eu; $CaMoO_4$:Mn,Eu; BaFBr:Eu; $Y_2O_2S$:Tb; $Y_2O_2S$:Er,Yb; $Y_2O_2S$:Er; $Y_2O_2S$:Eu; $Y_2O_3$:Eu; $Y_2O_3S$:Eu+$Fe_2O_3$; $Gd_2O_2S$:Tb; $Gd_2O_2S$:Eu; $Gd_2O_2S$:Nd; $Gd_2O_2S$:Yb,Nd; $Gd_2O_2S$:Yb,Tm; $Gd_2O_2S$:Yb, Tb; $Gd_2O_2S$:Yb,Eu; LaOF:Eu; $La_2O_2S$:Eu; $La_2O_2S$:Eu,Tb; $La_2O_2S$:Tb; $BaMgAl_{16}O_{27}$:Eu; $Y_2SiO_5$:Tb,Ce; $Y_3Al_5O_{12}$:Ce; $Y_3Al_{2.5}Ga_{2.5}O_{12}$:Ce; $YVO_4$:Nd; $YVO_4$:Eu; $Sr_5(PO_4)_3Cl$:Eu; CaS:Eu; ZnS:Ag; $ZnSiO_4$:Mn; $CaSiO_3$:Mn; ZnS:Bi; (Ca, Sr)S:Bi; $(Zn,Mg)F_2$:Mn; $CaWO_4$; $CaMoO_4$; ZnO:Zn; ZnO:Bi; and $KMgF_3$:Mn.

Visible light emitting compounds that are excited by exposure to UV radiation can be used including rare earth emitting compounds that are described in numerous publications including WO2007/051035 (Haushalter) that is incorporated herein by reference.

Examples of useful radioisotope marker materials include but are not limited to, $^{32}P$, $^3H$, $^{14}C$, $^{41}C$ $^{41}Ca$, $^{57}Co$ and $^{59}Fe$.

Examples of useful metal and metal-containing marker materials with different magnetic moments include but are not limited to, particles of iron, nickel, cobalt, and gadolinium, as well as particles of metal oxides, metal sulfides, metal oxysulfides, and metal oxyhydroxides. Other metal-containing compounds that would be useful as marker materials would be readily apparent to a skilled artisan. While many metal marker materials are insoluble in water or organic solvents, other metal marker materials are colloidal or suspendible materials in water or organic solvents.

Examples of infrared (IR) radiation absorbing compounds include compounds that emit infrared radiation having a wavelength of at least 700 nm and up to and including 1500 nm when irradiated with light having a shorter wavelength. Such compounds include but are not limited to, metal phthalocyanines, vanadyl phthalocyanines, copper phthalocyanines, metal free phthalocyanines, azines dyes, chlorophylls, and laser dyes.

Luminescing compounds that have the capability of being illuminated upon exposure to activating radiation include those described in EP 2,025,525 (noted above).

Examples of chemicals that can be used as marker materials and can then react when mixed include but are not limited to, isocyanates, amines, epoxies, carboxylic acids, hydroxyl compounds, silanes, silica, alumina and other such sols.

The various marker materials (including the first and second marker materials) can be present, independently, in an amount of up to and including 35 weight %, or at least 0.001 and up to and including 25 weight %, all based on total porous organic polymeric film weight. A skilled worker would understand that the various types of marker materials can be present in different amounts, depending for example on the amounts needed for detectability or the relative amounts of the marker materials needed in a specific porous organic polymeric film.

The solid porous organic polymeric film of the present invention can have an outer surface that has a contact angle with water that is at least 10° greater (or preferably at least 15° greater) than a nonporous organic polymeric film of the same composition and dry thickness.

The present invention provides at least the following embodiments and combinations thereof, but other combinations of features are considered to be within the present invention as a skilled artisan would appreciate from the teaching of this disclosure:

1. A method for preparing a porous organic polymeric film, the method comprising:
providing: (a) an aqueous phase comprising a cavity stabilizing hydrocolloid, and (b) an oil phase comprising a water-insoluble polymer or polymer precursor and an organic solvent,
dispersing the aqueous phase in the oil phase to form a water-in-oil emulsion,
applying the water-in-oil emulsion to a substrate to form a liquid coating containing droplets of the aqueous phase in the oil phase, and
removing the organic solvent from the oil phase and water from the aqueous phase, and polymerizing the polymer precursor if present, to form a porous organic polymeric film comprising a continuous polymeric solid phase, and multiple discrete cavities having inner walls and that are uniformly dispersed within the continuous polymeric solid phase,
wherein the porous organic polymeric film further comprises the cavity stabilizing hydrocolloid on the inner walls of the multiple discrete cavities.

2. The method of embodiment 1, wherein the oil phase further comprises a low HLB emulsifier that is eventually disposed at the interface of the multiple discrete cavities and the continuous polymeric solid phase of the porous organic polymeric film.

3. The method of embodiment 1 or 2, wherein the oil phase further comprises a low HLB emulsifier that is an amphiphilic block copolymer that is eventually disposed at the interface of the multiple discrete cavities and the continuous polymeric solid phase of the porous organic polymeric film.

4. The method of embodiment 3, wherein the amphiphilic block copolymer comprises a hydrophilic segment comprising polyethyleneoxide and an oleophilic segment comprising polycaprolactone.

5. The method of any of embodiments 1 to 4, wherein the cavity stabilizing hydrocolloid is carboxymethyl cellulose (CMC), a gelatin or gelatin derivative, a protein or protein derivative, a hydrophilic synthetic polymer, a water-soluble microgel, a polystyrene sulfonate, poly(2-acrylamido-2-methylpropane sulfonate, a polyphosphonate, or mixtures thereof.

6. The method of any of embodiments 1 to 5, wherein the cavity stabilizing hydrocolloid is present in an amount of at least 0.5 weight % and up to and including 20 weight %, based on total aqueous phase weight.

7. The method of any of embodiments 1 to 6, wherein the oil phase further comprises a low HLB emulsifier that is eventually disposed at the interface of the discrete cavities and the continuous polymeric solid phase of the porous organic polymeric film, which low HLB emulsifier is present in an amount of at least 0.2 weight % and up to and including 30 weight %, based on total oil phase weight.

8. The method of any of embodiments 1 to 7, wherein the porous organic polymeric film has an average dry thickness of at least 5 μm and up to and including 500 μm.

9. The method of any of embodiments 1 to 8, wherein the water-insoluble polymer is a polyester, styrenic polymer, acrylic polymer, mono-olefin polymer, vinyl ester polymer, α-methylene aliphatic monocarboxylic acid ester polymer, vinyl ether polymer, vinyl ketone polymer, aliphatic cellulose ester polymer, and mixtures of these materials.

10. The method of any of embodiments 1 to 9, wherein the total volume of the multiple discrete cavities is a least 5% and up to and including 80%, based on total solid porous organic polymeric film dry volume.

11. The method of any of embodiments 1 to 10, comprising dispersing the aqueous phase in the oil phase by homogenization to form a water-in-oil emulsion.

12. The method of any of embodiments 1 to 11, wherein the water-in-oil emulsion is coated on a substrate to form a liquid precursor porous organic polymeric film.

13. The method of embodiment 12, further comprising removing the water from the aqueous phase droplets before or after removing the organic solvent from the oil phase of the liquid precursor porous organic polymeric film.

14. The method of any of embodiments 1 to 13, wherein the multiple discrete cavities have an average size of at least 100 nm and up to and including 5 μm.

15. The method of any of embodiments 1 to 14, wherein the organic solvent is selected from the group consisting of ethyl acetate, propyl acetate, chloromethane, dicloromethane, vinyl chloride, trichloromethane, carbon tetrachloride, ethylene chloride, trichloroethane, toluene, xylene, cyclohexanone, dimethyl carbonate, 2-nitropropane, and mixtures of two or more of these compounds.

16. The method of any of embodiments 1 to 15, wherein the polymer precursor is an ethylenically unsaturated polymerizable monomer.

17. The method of embodiment 16, wherein the polymer precursor is an ethylenically unsaturated polymerizable monomer selected from vinyl monomers and acrylic monomers.

18. The method of any of embodiments 1 to 15, wherein the water-insoluble polymer is a styrene-butyl acrylate copolymer, polycaprolactone, polyurethane, or bisphenol-A polyester.

19. The method of any of embodiments 1 to 18, wherein the porous organic polymeric film comprises first and second discrete cavities that are isolated from each other and dispersed within the continuous polymeric solid phase, the first discrete cavities comprising a first marker material, and the second discrete cavities comprising a second marker material, which first and second marker materials are detectably different.

20. A porous organic polymeric film prepared from any of the embodiments 1 to 19, the porous organic polymeric film comprising a water-insoluble polymer that provides a continuous polymeric solid phase, and multiple discrete cavities having inner walls and that are uniformly dispersed within the continuous polymeric solid phase, wherein the porous organic polymeric film further comprises a cavity stabilizing hydrocolloid on the inner walls of the multiple discrete cavities.

21. The porous organic polymeric film of embodiment 20, further comprising a low HLB emulsifier that is disposed at the interface of the multiple discrete cavities and the continuous polymeric solid phase of the porous organic polymeric film.

22. The porous organic polymeric film of embodiment 20 or 21, further comprising a low HLB emulsifier that is an amphiphilic block copolymer that is disposed at the interface of the multiple discrete cavities and the continuous polymeric solid phase of the porous organic polymeric film.

23. The porous organic polymeric film of embodiment 22, wherein the amphiphilic block copolymer comprises a hydrophilic segment comprising polyethyleneoxide and an oleophilic segment comprising polycaprolactone.

24. The porous organic polymeric film of any of embodiments 20 to 23, wherein the cavity stabilizing hydrocolloid is carboxymethyl cellulose (CMC), a gelatin or gelatin derivative, a protein or protein derivative, a hydrophilic synthetic polymer, a water-soluble microgel, a polystyrene sulfonate, poly(2-acrylamido-2-methylpropane sulfonate, a polyphosphonate, or mixtures thereof.

25. The porous organic polymeric film of any of embodiments 20 to 24, wherein the cavity stabilizing hydrocolloid is present in an amount of at least 0.5 weight % and up to and including 20 weight %, based on total solid porous organic polymeric film dry weight.

26. The porous organic polymeric film of any of embodiments 20 to 25, further comprising a low HLB emulsifier that is disposed at the interface of the multiple discrete cavities and the continuous polymeric solid phase of the porous organic polymeric film, which low HLB emulsifier is present in an amount of at least 1 weight % and up to and including 99.5 weight %, based on total porous organic polymeric film dry weight.

27. The porous organic polymeric film of any of embodiments 20 to 26 that average dry thickness of at least 2 μm and up to and including 500 μm.

28. The porous organic polymeric film of any of embodiments 20 to 27, wherein the water-insoluble polymer is a polyester, styrenic polymer, acrylic polymer, mono-olefin polymer, vinyl ester polymer, α-methylene aliphatic monocarboxylic acid ester polymer, vinyl ether polymer, vinyl ketone polymer, aliphatic cellulose ester polymer, and mixtures of these materials.

29. The porous organic polymeric film of any of embodiments 20 to 28, wherein the multiple discrete cavities have an average size of at least 200 nm and up to and including 5 μm.

30. The porous organic polymeric film of any of embodiments 20 to 29, wherein the water-insoluble polymer is a styrene-butyl acrylate copolymer, polycaprolactone, polyurethane, or bisphenol-A polyester.

31. The solid porous organic polymeric film of any of embodiments 20 to 30 that is disposed on a substrate.

32. The solid porous organic polymeric film of any of embodiments 20 to 31 having a reflectance of that is at least 6 times greater than a solid nonporous film composed of the same composition and dry thickness.

33. The porous organic polymeric film of any of embodiments 20 to 32, wherein at least some of the multiple discrete cavities comprise an aqueous solution or suspension of an organic catalytic material or nanoparticles of catalytically active metallic materials, wherein the porous organic polymeric film is impermeable to the organic catalytic material and nanoparticles of catalytically active metallic materials, and the porous organic polymeric film is permeable to molecules having a molar mass that is 1000 Daltons or less.

34. The porous organic polymeric film of embodiment 33, wherein at least some of the multiple discrete cavities comprise the organic catalytic material that is an enzyme.

35. The porous organic polymeric film of embodiment 33, wherein at least some of the multiple discrete cavities comprise the nanoparticles of catalytically active metallic materials, which nanoparticles (a) comprise one or more elements selected from Groups 8, 9, 10, and 11 of the Periodic Table, and (b) have an effective diameter of at least 1 nm and up to and including 200 nm.

36. The solid porous organic polymeric film of any of embodiments 20 to 35 having an outer surface that has a contact angle with water that is at least 10° greater than a solid nonporous organic polymeric film of the same composition and dry thickness.

37. The solid porous organic polymeric film of any of embodiments 20 to 32, comprising first and second discrete cavities that are isolated from each other and dispersed within the continuous polymeric solid phase, the first discrete cavities comprising a first marker material, and the second discrete cavities comprising a second marker material, which first and second marker materials are detectably different.

The following Examples are provided to illustrate the practice of this invention and are not meant to be limiting in any manner.

The following materials used in the Examples:

Polycaprolactone (PCL), molecular weight 45,000, was obtained from Sigma Aldrich Company.

NeoCryl® B723, a copolymer derived from butyl methacrylate and methyl methacrylate, and Solsperse 43,000, a 50% active alkylphenol ethoxylated (APE)-free polymeric dispersant in water, were both obtained from Noveon/Lubrizol.

The polyesters, Kao E and Kao N were obtained from Kao Specialties Americas LLC, a part of Kao Corporation (Japan).

Polyurethane (PU-5, acid number 5, molecular weight 67,000) derived from polycaprolactone diol and isophorone diisocyanate was prepared using known procedures and starting materials.

Polyurethane (PU-E, molecular weight 40,000) end-capped with methoxy polyethylene oxide derived from polycaprolactone diol and isophorone diisocyanate was prepared using known procedures and starting materials.

Piccotoner® 1221, a polymer derived from styrene and butyl acrylate was obtained from Hercules-Sanyo, Inc. (Wilmington, Del.).

Carboxy methylcellulose ($M_n$=250,000) was obtained from Acros Organics or from Ashland Aqualon as Aqualon 9M31F. These products were used interchangeably.

Amphiphilic block copolymers of polyethylene oxide and polycaprolactone (PEO-b-PCL) were prepared using the procedure described in U.S. Pat. No. 5,429,826 (Nair et al.). The amphiphilic block copolymer emulsifiers were designed to have the following molecular weights in the block components where the first number is the molecular weight of the hydrophilic block segment and the second number is the molecular weight of the oleophilic block segment: 5,000-20,000, 5,000-25,000, and 750-45,000.

GRINDSTED® PGPR 90, polyglycerol polyricinolate emulsifier, can be obtained from Dupont.

Poly(ethyleneimine), 50 weight % in water was obtained from Eastman Kodak Company.

The marker materials used with some porous organic polymeric films of this invention were cyan and magenta pigments. The cyan (C) pigment PB 15:3 (Sunfast Blue 15:3) was obtained from Sun Chemicals. The magenta (M) pigment PR 185 (Graphtol Carmine HF4C) was obtained from Clariant. These pigments were milled in water using dispersants prior to incorporation in the aqueous phase. The cyan "millgrind" (CM) was made using Solsperse® 43000 (30 weight % with respect to pigment) as the dispersant at 19 weight % of pigment. The magenta "millgrind" (MM) was made using Disperbyk® 190 (20 weight % with respect to pigment) as the dispersant at 15 weight % of pigment.

The porous organic polymeric films of this invention were coated on one or more of the following substrates. Porous organic polymeric films were obtained from the water-in-oil emulsions described below by coating the emulsions onto the various substrates using various coating knives. The coatings were dried under ambient conditions with controlled temperatures.

Substrate 1 was a 0.1 mm poly(ethylene terephthalate) (PET) film coated with a subbing layer comprising a terpolymer derived from acrylonitrile, vinylidene chloride and acrylic acid.

Substrate 2 was Substrate 1 overcoated with poly(ethyleneimine).

Substrate 3 was the same as Substrate 1 but the subbing layer comprised a copolymer derived of glycidyl methacrylate and butyl acrylate.

Other substrates used were unsubbed PET (no, subbing layer) and a 0.8 mm Teflon sheet.

The particle size of the water-in-oil emulsions comprising the coating compositions were measured using the Malvern Zetasizer, and the reported sizes were the mean sizes.

To further characterize the discrete cavity sizes within a given porous organic polymeric film, representative scanning electron micrographs were taken of porous organic polymeric films and simple image analysis routines were used to first identify the discrete cavities within and then to measure the diameter of the discrete cavities. A commercial statistical analysis software package was then used to study the distribution of the discrete cavities within each porous organic polymeric film.

Control 1

Nonporous Organic Polymeric Film of PCL

An oil phase (50 g) containing 15 weight % of polycaprolactone and 5 weight % of PEO-b-PCL (750-45,000) in ethyl acetate was coated on a Teflon sheet at a 0.025 cm wet lay down and dried under ambient conditions to form a nonporous organic polymeric film that had a thickness of 10 μm with no cavities observable using microscopic methods.

Invention Example 1

Porous Organic Polymeric Film of PCL

An oil phase (50 g) was prepared using 30 g of a 25 weight % solution of PCL and 20 g of a 12.5 weight % solution of PEO-b-PCL (750-45,000) in ethyl acetate. This oil phase was homogenized with an aqueous phase prepared with 15 g of a 2 weight % solution of carboxy methyl cellulose at very high shear with a Silverson L4R Mixer (sold by Silverson Machines, Inc.) followed by homogenization in a Microfluidizer Model #110T from Microfluidics to give a water-in-oil emulsion with water droplets of the size of 0.82 μm. The resulting water-in-oil emulsion was coated onto Substrate 3 at a 0.01 cm wet lay down and dried under ambient conditions to yield a porous organic polymeric film of this invention having an average cavity size of 2 μm.

Invention Example 2

Porous Organic Polymeric Film of Piccotoner 1221

An oil phase was prepared using 125 g of a 20 weight % solution of Piccotoner 1221 and 1 g of GRINSTED® PGPR 90 in ethyl acetate. This oil phase was homogenized with an aqueous phase prepared with 35.5 g of a 2 weight % solution of carboxy methyl cellulose in water also containing 0.2 weight % of poly(ethyleneimine). A porous organic polymeric film of this invention was prepared as described above for Invention Example 1 and had an average pore size of 2 μm.

Invention Example 3

Porous Organic Polymeric Film of NeoCryl® B723

An oil phase was prepared using 50 g of a 20 weight % solution of NeoCryl® B723 and 0.4 g of GRINSTED® PGPR 90 in ethyl acetate. This oil phase was homogenized with an aqueous phase prepared with 15 g of a 2 weight % solution of carboxy methyl cellulose at very high shear with a Silverson L4R Mixer (sold by Silverson Machines, Inc.) followed by homogenization in a Microfluidizer Model #110T from Microfluidics to give a water-in-oil emulsion. A porous organic polymeric film of this invention was prepared as described above in Invention Example 1 except that it was coated at 10° C. on Substrate 1 and the film had an average cavity size of 2 μm.

Invention Example 4

Porous Organic Polymeric Film of PU-5

A water-in-oil emulsion was prepared as in Invention Example 1 except the 50 g of oil phase comprised a 20 weight % solution of polyurethane (PU-5) and a 1.4 weight % solution of PEO-b-PCL (5,000-25,000) as the emulsifier in ethyl acetate. A porous organic polymeric film of this invention was prepared by coating the water-in-oil emulsion on Substrate 2 at a 0.01 cm wet lay down and dried under ambient conditions to yield a film that had an average cavity size of 0.5 μm.

Invention Example 5

Porous Organic Polymeric Film of PU-E

A water-in-oil emulsion was prepared as in Invention Example 1 except the emulsion was prepared using an oil phase comprising a 20 weight % solution of polyurethane (PU-E) in ethyl acetate and no emulsifier. The water-in-oil emulsion was coated onto Substrate 2 at a 0.01 cm wet lay down and dried under ambient conditions to form a porous organic polymeric film of this invention that had an average cavity size of 0.5 μm.

Invention Example 6

Porous Organic Polymeric Film of Kao E

A water-in-oil emulsion was prepared as in Invention Example 5 except that the polyester Kao E was used in place of the polyurethane and the resulting water-in-oil emulsion was coated onto unsubbed PET to form a porous organic polymeric film of this invention having an average cavity size of 0.6 μm.

Invention Example 7

Porous Organic Polymeric Film of Kao N

A water-in-oil emulsion was prepared as in Invention Example 6 except Kao N polyester was used and the water-in-oil emulsion was coated onto Substrate 1 to provide a porous organic polymeric film of this invention that had an average cavity size of 1.25 μm.

Opacity of Porous Organic Polymeric Films:

Opacity is essentially the hiding power of the coating or the degree to which something will hide what is underneath it. Opacity measurements were made of various porous organic polymeric films that were applied to paper stock substrates with black and white patches (Leneta Form 2C Opacity chart) using an integrating sphere and XRite SP60 Spectrophotometer in opacity mode with D65 and 2° observer. The measurements were compared to nonporous organic polymer films coated on the same paper stock substrates.

Control 2

Nonporous Organic Polymeric Film of PCL

An oil phase (20 g) containing 20 weight % of polycaprolactone in ethyl acetate was coated on a Leneta Opacity Chart 2C at a 0.008 cm wet lay down and dried under ambient conditions to form a nonporous organic polymeric film that was translucent.

Control 3

Nonporous Organic Polymeric Film of NeoCryl® B723

An oil phase (20 g) containing 20 weight % of NeoCryl® B723 in ethyl acetate was coated on a Leneta Opacity Chart 2C as in Control 2 to form a nonporous organic polymeric film that was clear.

Invention Example 8

Porous Organic Polymeric Film of PCL

A water-in-oil emulsion was prepared as in Invention Example 1 except that the emulsion was coated onto Leneta Opacity Chart 2C at a 0.008 cm wet lay down and dried under ambient conditions to form a white, opaque porous organic polymeric film.

Invention Example 9

Porous Organic Polymeric Film of NeoCryl® B723

A water-in-oil emulsion was prepared as in Invention Example 3 except the emulsion was coated onto Leneta Opacity Chart 2C at a 0.008 cm wet lay down and dried under ambient conditions to form a white, opaque porous organic polymeric film.

The results of the opacity measurements from Invention Examples 8 and 9 are shown below in TABLE I and show that the porous organic polymeric films of this invention scatter visible light and exhibit more opacity than the nonporous organic polymeric films described in Controls 2 and 3.

TABLE I

| Article | Organic Polymeric Film | Wet Films (cm) | Opacity |
| --- | --- | --- | --- |
| Control 2 | Nonporous | 0.008 | 24.49 |
| Invention Example 8 | Porous | 0.008 | 68.57 |
| Control 3 | Nonporous | 0.008 | 5.53 |
| Invention Example 9 | Porous | 0.008 | 54.08 |

Invention Example 10

Porous Organic Polymeric Film of PCL

A water-in-oil emulsion was prepared as in Invention Example 8 except that the water-in-oil emulsion was coated onto a plasma treated transparent polypropylene substrate at a 0.025 cm wet lay down to form a white, opaque porous organic polymeric film of the present invention. The reflectance and transmission of the resulting article compared to the uncoated transparent substrate were analyzed using a PerkinElmer Instruments, Lambda 800, UV/VIS Spectrometer. The porous organic polymeric film of Invention Example 10 was found to have a reflectance that was at least 6 times greater than reflectance of the uncoated transparent substrate and a transmission that was at least 6 times lower than that of the uncoated transparent substrate.

Porous Organic Polymeric Films Containing Catalytic Materials:

The palladium nanoparticles used in the following example were prepared by the method described in *J. Phys. Chem. B* 2001, 105, 8938-8943.

Invention Example 11

Porous Organic Polymeric Film of PCL Containing Pd Nanoparticles

Pd nanoparticles were encapsulated in a water-in-oil emulsion prepared as described above for Invention Example 1 using 33 g of a 3.4 weight % CMC solution and 25 g of a 0.2 weight % Pd nanoparticles in water as the aqueous phase, and 187 g of a 6.5 weight % polycaprolactone (PCL) and 1.4 weight % PEO-b-PCL (5,000-25,000) in ethyl acetate. The water phase and oil phase were homogenized and the water-in-oil emulsion was then coated on Substrate 1 at a 0.01 cm wet lay down and dried under ambient conditions to yield a porous organic polymeric film of this invention containing Pd nanoparticles (0.82 μg/cm²) in the multiple discrete cavities of the porous film as determined using Inductively Coupled Plasma Atomic Emission Spectroscopy (ICP-AES).

The activity of Pd nanoparticles in the porous organic polymeric film of this invention was confirmed by following the UV absorbance of hydrogen peroxide with time to monitor its uptake and decomposition by the Pd nanoparticles in the porous organic polymeric film. The results showed increased consumption of hydrogen peroxide by the Pd nanoparticles in the porous organic polymeric film compared to a porous organic polymeric film that did not contain Pd nanoparticles (Invention Example 3) that corresponded to the amount of Pd nanoparticles in the cavities.

Invention Example 12

Hydrogenation of 2-Butyne-1,4-diol using Porous Organic Polymeric Film of PCL Containing Pd Nanoparticles A strip of coating 2 cm wide×10 cm long provided according to Invention Example 11 was cut and placed into a 500 ml Parr bottle reactor. To the bottle reaction were added 50 g of water and 1 g of 2-butyne-1,4-diol reactant (12 mmol). Hydrogen was introduced at 46 psi (317 kPa) to the bottle reactor and the mixture was shaken continuously at ambient temperature. Periodically, small aliquots were removed for analysis by gas chromatography (GC). After each aliquot was taken, the mixture was re-pressurized with hydrogen, and the reaction was continued. The concentrations of the reactant and the resulting hydrogenation product, 2-butene-1,4-diol, were determined by GC of the samples as shown in below in TABLE II.

TABLE II

| Time (minutes) | [2-Butyne-1,4-diol] | [2-Butene-1,4-diol] |
|---|---|---|
| 0 | 100% | 0% |
| 91 | 97.1% | 2.8% |
| 179 | 95.0% | 4.9% |
| 270 | 93.0% | 6.8% |
| 345 | 90.9% | 8.9% |

These results show that the Pd nanoparticles in the multiple discrete cavities of the porous organic polymeric film of the present invention were capable of catalyzing hydrogenation reactions. After this reaction, the porous organic polymeric film was re-used by removing it from the hydrogenation vessel, rinsing it with water, and carrying out the same reaction with the same reactant under the same conditions. It was determined that the rate of catalytic reaction were the same as those determined for the first use of the porous organic polymeric film.

These results show that the same Pd nanoparticle loaded porous organic polymeric film of the present invention can be used effectively multiple times for the catalytic reaction (hydrogenation) of 2-butyne-1,4-diol.

Water Permeability of Free Standing Porous Organic Polymeric Films

Invention Example 13

Evaluation of Permeability of Porous Organic Polymeric Film of PCL

A free standing porous organic polymeric film of this invention was prepared by coating a water-in-oil emulsion described in Invention Example 1 onto a Teflon sheet (substrate) at a 0.025 cm wet lay down and then peeling off the dried porous organic polymeric film of this invention.

This porous organic polymeric film having a dry thickness of 10 μm was then cut using a 47 mm disc punch, and the resulting circular sample was then mounted in a filter holder attached to a pressurized reservoir to form a porous membrane. The membrane was first wetted with a 50% aqueous methanol solution by forcing 300 g of this solution through the membrane. This was followed by forcing 300 g of ultra-pure water through the membrane at 1.5 psi (10.3 kPa), and the time and weight of permeate were recorded. The flow rate characteristic at which the water flowed through the membrane was compared to a membrane similarly prepared using the Control 1 nonporous organic polymeric film. The porous organic polymeric film of this invention showed a steady rate of water permeation with an average flow rate of 14 g/min while the Control 1 nonporous showed no measurable water permeability.

Hydrophobicity of Porous Organic Polymeric Films

Control 4

Nonporous Organic Polymeric Film of Kao N

An oil phase (20 g) containing 20 weight % of Kao N polyester in ethyl acetate was coated onto Substrate 1 at a 0.01 cm wet lay down at 10° C. to form a nonporous organic polymeric film.

Invention Example 15

Evaluation of Hydrophobicity of Porous Organic Polymeric Film of Kao N

A water-in-oil emulsion was prepared as in Invention Example 7 except the porous organic polymeric film was prepared at 10° C. The water contact angle of this porous organic polymeric film and the nonporous organic polymeric film of Control 4 were measured using ultra pure water in a Ramé-Hart goniometer. The water contact angle of the porous organic polymeric film of Invention Example 15 was determined to 92.5° compared to 80° determined for the Control 4 nonporous organic polymeric film. This clearly shows greater hydrophobicity for a porous organic polymeric film of the present invention.

Porous Organic Polymeric Films Containing Marker Materials in Separate Discrete Cavities Invention Example 16

Porous Organic Polymeric Films of NeoCryl® B723 containing Cyan and Magenta Marker Materials in Separate Discrete Cavities An oil phase (100 g) was prepared using 100 g of a 20 weight % solution of NeoCryl® B723 in ethyl acetate containing 0.8 g of GRINSTED® PGPR 90. This oil phase was homogenized with an aqueous phase prepared with 15.2 g of CM marker and 0.4 g of carboxy methyl cellulose in 4.4 g of water as described in Invention Example 1, to yield a cyan marker-containing water-in-oil emulsion. A magenta marker-containing water-in-oil emulsion was similarly prepared using the same oil phase and an aqueous phase containing 20 g of MM marker and 0.4 g of carboxy methyl cellulose. The cyan marker-containing water-in oil emulsion (1 g) and the magenta marker-containing water-in-oil emulsion (1 g) were added to 100 g of an oil phase prepared as described above and the composite water-in-oil emulsion was coated as described in Invention Example 1 onto Substrate 1. The resulting dried porous organic polymeric film had clearly visible cyan and magenta markers in separate discrete pores as observed at a magnification of 600×.

The invention has been described in detail with particular reference to certain preferred embodiments thereof, but it will be understood that variations and modifications can be effected within the spirit and scope of the invention.

The invention claimed is:

1. A method for preparing a porous organic polymeric film, the method comprising:
   providing: (a) an aqueous phase comprising a cavity stabilizing hydrocolloid, and (b) an oil phase comprising a water-insoluble polymer or polymer precursor and an organic solvent,
   dispersing the aqueous phase in the oil phase to form a water-in-oil emulsion,
   applying the water-in-oil emulsion to a substrate to form a wet coating containing droplets of the aqueous phase in the oil phase, and
   removing the organic solvent from the oil phase and water from the aqueous phase, and polymerizing the polymer precursor if present, to form a porous organic polymeric film comprising a continuous polymeric solid phase, and multiple discrete cavities having inner walls and that are uniformly dispersed within the continuous polymeric solid phase,
   wherein the porous organic polymeric film further comprises the cavity stabilizing hydrocolloid on the inner walls of the multiple discrete cavities.

2. The method of claim 1, wherein the oil phase further comprises an emulsifier having a hydrophilic-lipophilic balance value equal to or less than 6, which emulsifier is eventually disposed at the interface of the multiple discrete cavities and the continuous polymeric solid phase of the porous organic polymeric film.

3. The method of claim 2, wherein the emulsifier in the oil phase is an amphiphilic block copolymer.

4. The method of claim 3, wherein the amphiphilic block copolymer comprises a hydrophilic segment comprising polyethyleneoxide and an oleophilic segment comprising polycaprolactone.

5. The method of claim 1, wherein the cavity stabilizing hydrocolloid is carboxymethyl cellulose (CMC), a gelatin or gelatin derivative, a protein or protein derivative, a hydrophilic synthetic polymer, a water-soluble microgel, a polystyrene sulfonate, poly(2-acrylamido-2-methylpropane sulfonate, a polyphosphonate, or mixtures thereof.

6. The method of claim 1, wherein the cavity stabilizing hydrocolloid is present in an amount of at least 0.1 weight % and up to and including 30 weight %, based on total aqueous phase weight.

7. The method of claim 2, wherein the emulsifier is present in the oil phase is present in an amount of at least 1 weight % and up to and including 100 weight %, based on total oil phase weight.

8. The method of claim 1, wherein the porous organic polymeric film has an average dry thickness of at least 5 µm and up to and including 500 µm.

9. The method of claim 1, wherein the water-insoluble polymer is a polyester, styrenic polymer, acrylic polymer, mono-olefin polymer, vinyl ester polymer, α-methylene aliphatic monocarboxylic acid ester polymer, vinyl ether polymer, vinyl ketone polymer, aliphatic cellulose ester polymer, and mixtures of these materials.

10. The method of claim 1, wherein the total volume of the multiple discrete cavities is a least 5% and up to and including 80%, based on total solid porous organic polymeric film dry volume.

11. The method of claim 1, comprising dispersing the aqueous phase in the oil phase by homogenization to form a water-in-oil emulsion.

12. The method of claim 1, wherein the water-in-oil emulsion is coated on a substrate to form a liquid precursor porous organic polymeric film.

13. The method of claim 1, further comprising removing the water from the aqueous phase droplets before or after removing the organic solvent from the oil phase of the liquid precursor porous organic polymeric film.

14. The method of claim 1, wherein the multiple discrete cavities have an average size of at least 200 nm and up to and including 5 µm.

15. The method of claim 1, wherein the organic solvent is selected from the group consisting of ethyl acetate, propyl acetate, chloromethane, dichloromethane, vinyl chloride, trichloromethane, carbon tetrachloride, ethylene chloride, trichloroethane, toluene, xylene, cyclohexanone, dimethyl carbonate, 2-nitropropane, and mixtures of two or more of these compounds.

16. The method of claim 1, wherein the polymer precursor is an ethylenically unsaturated polymerizable monomer.

17. The method of claim 1, wherein the polymer precursor is an ethylenically unsaturated polymerizable monomer selected from vinyl monomers and acrylic monomers.

18. The method of claim 1, wherein the water-insoluble polymer is a styrene-butyl acrylate copolymer, polycaprolactone, polyurethane, or bisphenol-A polyester.

* * * * *